(12) United States Patent
Dan et al.

(10) Patent No.: US 8,212,109 B2
(45) Date of Patent: Jul. 3, 2012

(54) METHOD FOR THE PRODUCTION OF TRANSGENIC PLANTS

(75) Inventors: Yinghui Dan, Wildwood, MO (US); Joyce E. Fry, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1205 days.

(21) Appl. No.: 10/064,001

(22) Filed: Jun. 3, 2002

(65) Prior Publication Data

US 2003/0110531 A1 Jun. 12, 2003

Related U.S. Application Data

(60) Provisional application No. 60/306,593, filed on Jul. 19, 2001.

(51) Int. Cl.
*A01H 1/00* (2006.01)
*C12N 15/82* (2006.01)
*C12N 15/87* (2006.01)

(52) U.S. Cl. ......... 800/278; 800/279; 800/293; 800/294

(58) Field of Classification Search ................. 800/279, 800/320.3, 278, 293, 294; 504/116.1
See application file for complete search history.

(56) References Cited

U.S. PATENT DOCUMENTS

| 5,631,152 | A | * | 5/1997 | Fry et al. ...................... 800/268 |
| 736,369 | A | | 4/1998 | Bowen et al. |
| 5,736,369 | A | * | 4/1998 | Bowen et al. .................. 800/293 |
| 5,767,368 | A | | 6/1998 | Zhong et al. |
| 5,932,782 | A | | 8/1999 | Bidney |
| 5,969,213 | A | | 10/1999 | Adams et al. |
| 6,020,539 | A | | 2/2000 | Goldman et al. |
| 6,995,016 | B2 | * | 2/2006 | Eudes et al. ............... 435/430.1 |

FOREIGN PATENT DOCUMENTS

| WO | WO 95/06127 | 3/1995 |
| WO | WO 96/04392 | 2/1996 |
| WO | WO 97/48814 | 12/1997 |
| WO | WO 98/51806 | 11/1998 |

OTHER PUBLICATIONS

Kless et al., Improvement of Plant Regeneration and GUS Expression in Scutellar Wheat Calli by Optimization of Culture Conditions and DNA-Microprojectile Delivery Procedures, Mol. Gen. Genet. (1992), 235:279-284.*
Wu et al., Factors Influencing Successful Agrobacterium-Mediated Genetic Transformation of Wheat, Plant Cell Rep., 21:659-668, 2003.*
Sahrawat AK et al., Genetic Improvement of Wheat Via Alien Gene Transfer, an assessment, Plant Science (2003), 165:1147-1168.*
Zhou et al. 1995 Plant Cell Reports 15: 159-163.*
Tegeder et al. 1995. Plant Cell Reports 15: 164-169.*
Weeks et al. 1993. Plant Physiol. 102: 1077-1084.*
Cheng et al. 1997. Plant Physiol. 115: 971-980.*
King et al. Dictionary of Genetics, 5th ed., 1997, p. 121.*
Poehlman et al. 1995. Molecular biology: Application in plant breeding, Chapter 8. In Breeding Field Crops, 4th ed., pp. 132-155.*
Cheng et al. 1997. Plant Physiol 115: 971-980.*
Zhong et al. 1992. Planta 187: 483-489.*
Cheng et al. 1997. Plant Physiology 115: 971-980.*
Bartok et al. 1990. Plant Cell, Tissue and Organ Culture 22: 37-41.*
Weeks et al. 1993. Plant Physiol 102: 1077-1084.*
Francis et al., The plant cell cycle, *Physiologia Plantarium* 93:365-374 (1995).
Leduc et al., Gene transfer to inflorescence and flower meristems using ballistic micro-targeting, *Sexual Plant Reproduction* 7:135-143 (1994).
Sautter et al., Ballistic Microtargeting of Visible Marker Genes to the Shoot Meristem of Wheat, *In Potrykus and Spangenberg* (eds), pp. 152-156 (1994).
Sautter et al., Shoot apical meristems as a target for gene transfer by micro ballistics, *Euphyticac* 85:45-51 (1995).
Terada et al., A type I element composed of the hexamer (ACGTCA) and octamer (CGCGGATC) motifs plays a role(s) in meristematic expression of a wheat histone H3 gene in transgenic rice plants, *Plant Molecular Biology* 27:17-26 (1995).

* cited by examiner

*Primary Examiner* — Anne Grunberg
*Assistant Examiner* — Keith Robinson
(74) *Attorney, Agent, or Firm* — SNR Denton US LLP; Thomas P. McBride Esq.

(57) ABSTRACT

Mesocotyl meristem explants that contain multiple primary meristems are transformed via particle bombardment or Agrobacterium-mediated methods. Regeneration is through an organogenesis pathway that allows for secondary multiple bud formation. This method allows for the genotype independent transformation of varieties of wheat.

12 Claims, 4 Drawing Sheets

METHOD FOR THE PRODUCTION OF TRANSGENIC PLANTS

This application claims the priority of U.S. Provisional Application No. 60/306,593, filed on Jul. 19, 2001, the entire disclosure of which is incorporated herein by reference.

BACKGROUND OF INVENTION

The present invention relates to the field of plant biotechnology. More specifically, it concerns methods of transformation and regeneration of plants. In particular, provided herein is an efficient, reproducible system for transforming and regenerating wheat.

In recent years, there has been a tremendous expansion of the capabilities for the genetic engineering of plants. Production of transgenic plants is dependent on achieving both stable integration of DNA into the genome of plant cells and regeneration from transformed cells of phenotypically normal, fertile adult plants. It remains an object for those skilled in the art to develop novel or improved methods for the production of transgenic plants; especially in those species with great commercial value.

SUMMARY OF INVENTION

According to the present invention there is provided a method of producing a transgenic plant comprising culturing an explant presenting a plurality of meristems on a media suitable to induce multiple buds from at least one or more of the meristems and introducing exogenous DNA into at least one of the cells of the multiple buds to generate transformed buds. Subsequently, the transformed buds are cultured on a media capable of inducing regeneration of plants from the transformed cells of the buds. In a preferred embodiment, the multiple bud inducing media comprises a combination of thidiazuron (TDZ) and an auxin. In another aspect of the invention, the explant is a mesocotyl explant, which comprises an apical meristem and several axillary meristems including the scutellar node meristem. Within the method of this invention, primary and axillary meristems are induced to generate multiple secondary buds by culturing on an appropriate medium, and subsequently, the secondary bud tissue is transformed and regenerated into whole, fertile, transgenic plants.

DETAILED DESCRIPTION

The following definitions will aid in the understanding of the description of the invention.

"Callus" refers to an undifferentiated proliferating mass of cells or tissue in vitro, "Plastid genome" refers to the genetic information of a plastid, which occurs as multiple copies of a circular, double stranded DNA molecule.

"Coding sequence" or "open reading frame" refers to a region of continuous sequential nucleic acid triplets encoding a protein, polypeptide, or peptide sequence.

"Dicot" or "dicotyledonous" refers to plants that produce an embryo with two cotyledons. Examples of dicots include cotton, soybean and peanut.

"Endogenous" refers to materials originating from within the organism or cell.

"Exogenous" refers to materials originating from outside of the organism or cell. It refers to nucleic acid molecules used in producing transformed or transgenic host cells and plants. As used herein, exogenous is intended to refer to any nucleic acid that is introduced into a recipient cell, regardless of whether a similar nucleic acid may already be present in such cell.

"Genome" refers to the chromosomal DNA of an organism. The genome is defined as a haploid set of chromosomes of a diploid species. For the purposes of this application, genome also includes the "plastid genome."

"Monocot" or "monocotyledonous" refers to plants having a single cotyledon. Examples include cereals such as maize, rice, wheat, oat, and barley.

"Primary meristem" refers to the apical meristem. "Axillary meristem" refers to the scutellar node meristem, coleoptile node bud, first leaf bud, and leaf node meristems. All of these meristems can be observed in a developing embryo, seedling, or plant.

"Nucleic acid" refers to deoxyribonucleic acid (DNA) or ribonucleic acid (RNA).

"Phenotype" refers to a trait exhibited by an organism resulting from the interaction of genotype and environment.

"Polyadenylation signal" or "polyA signal" refers to a nucleic acid sequence located 3' to a coding region that promotes the addition of adenylate nucleotides to the 3' end of the mRNA transcribed from the coding region.

"Promoter" or "promoter region" refers to a nucleic acid sequence, usually found 5' to a coding sequence, that controls expression of the coding sequence by controlling production of messenger RNA (mRNA) by providing the recognition site for RNA polymerase or other factors necessary for the start of transcription at the correct site.

"Recombinant nucleic acid vector" or "vector" refers to any agent such as a plasmid, cosmid, virus, autonomously replicating sequence, phage, or linear or circular single- or double-stranded DNA or RNA nucleotide segment, derived from any source, capable of genomic integration or autonomous replication, comprising a nucleic acid molecule in which one or more nucleic acid sequences have been linked in a functionally operative manner. Such recombinant nucleic acid vectors or constructs are capable of introducing a 5' regulatory sequence or promoter region and a DNA sequence for a selected gene product into a cell in such a manner that the DNA sequence is transcribed into a functional mRNA, which is subsequently translated into a polypeptide or protein.

"Regeneration" refers to the process of growing a plant from a plant cell.

"Selectable marker" or "screenable marker" refers to a nucleic acid sequence whose expression confers a phenotype facilitating identification of cells containing the nucleic acid sequence.

"Transcription" refers to the process of producing an RNA copy from a DNA template.

"Transformation" refers to a process of introducing an exogenous nucleic acid sequence (vector or construct) into a cell or protoplast, in which that exogenous nucleic acid is incorporated into the nuclear DNA, plastid DNA, or is capable of autonomous replication.

"Transgenic" refers to organisms into which an exogenous nucleic acid sequence has been integrated.

The present invention relates to a method for producing a plant with exogenous DNA integrated into its nuclear genome or plastid genome. The invention is applicable to any species of plant, including monocot and dicot species, and has been found to be particularly useful for producing transgenic wheat plants.

An efficient method of producing transgenic plants includes an efficient means of introducing foreign DNA into the genome of the cells of the explant, and thereafter an efficient means of regenerating mature plants from the transformed cells. The present invention provides such a method of generating transgenic plants from explant tissue. The method of this invention generates multiple plants from a single explant via direct organogenesis. Organogenesis is a process of differentiation by which plant organs are formed de novo or from preexisting structures. In this method, the explants are cultured in a manner so as to produce multiple buds, and when cultured in a multiple shoot inducing media, these buds form shoots that can be grown into mature plants. In a preferred embodiment, the regenerable cells of the explant are transformed either prior to or during the process of regeneration prior to the elongation and rooting stages. This method has advantages over the existing methods. For example, organogenesis avoids the problems of embryogenesis by eliminating the callus phase, which can lead to somaclonal variation and is recognized in the art as genotype and species dependent. In addition, the present invention reduces the manipulations required to produce a transformed plant, and the explant utilized avoids the need for labor and space intensive cultivation of stock plants.

To initiate the process in accordance with the present invention, it is first necessary to select the starting material, or explant. Any regenerable cell or tissue may be utilized. Regenerable tissue is tissue that, under appropriate culture conditions, can give rise to a mature, fertile plant. In the present invention, meristematic tissue is the preferred explant. Meristem tissue is a tissue that produces cells that undergo differentiation to form mature tissues. Any type of vegetative meristem explant can be used in accordance with this invention, such as mesocotyl sections, hypocotyl sections, mature embryos and immature embryos that can be excised from seedlings, mature seeds or immature seeds. Particularly preferred for monocots, such as wheat, are explants comprising mesocotyl tissue including apical and axillary meristems, or explants such as mature or immature embryos. For dicots, such as cotton, particularly preferred explants include hypocotyl sections that include multiple meristems. As used herein, hypocotyl refers to the portion of an embryo or seedling between the cotyledons and the radical; mesocotyl refers to the internode between and including the scutellar node, and the coleoptile. It is also envisioned that other tissues that contain multiple meristems will be useful in the process.

Figure 1:
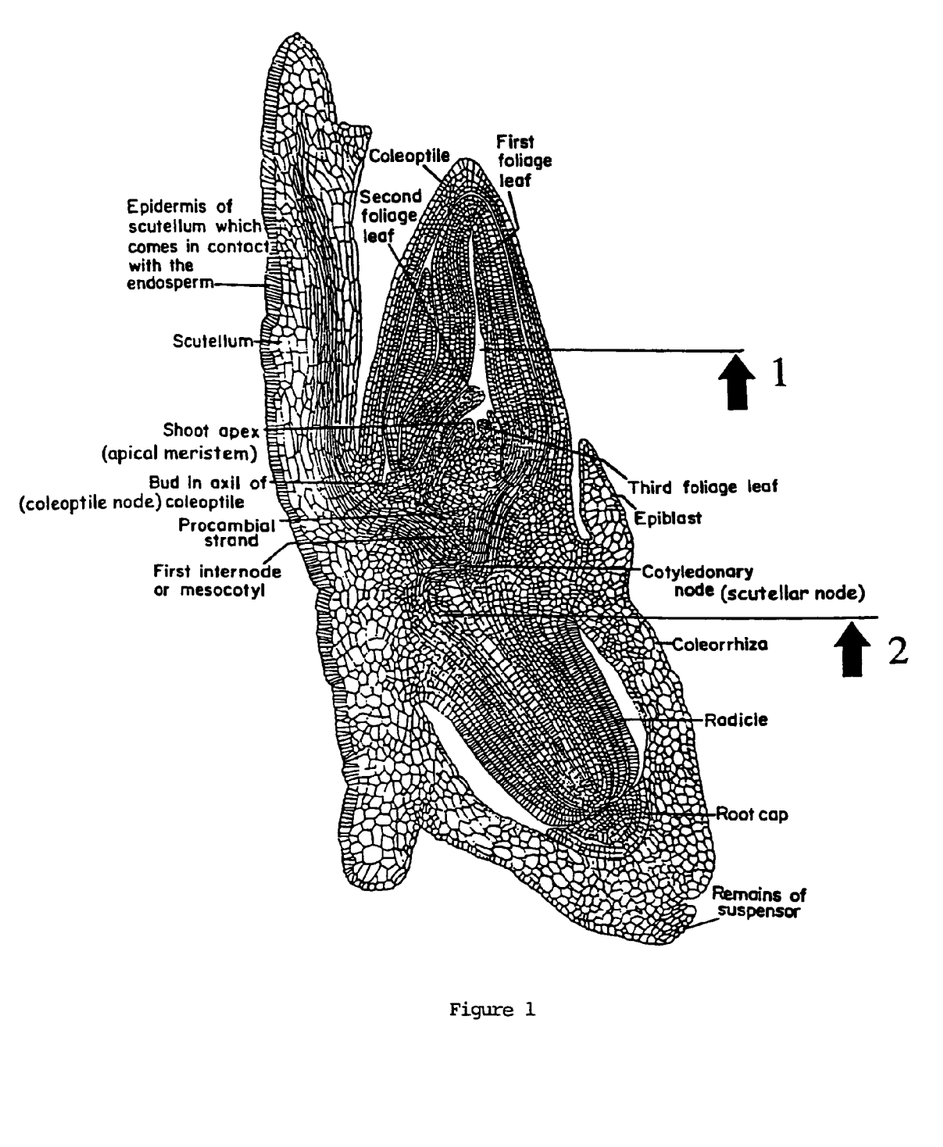
FIG. 1 is a longitudinal section of a mesocotyl explant. Arrow 1 indicates the approximate location of the cut made to remove the upper portion of the coleoptile. Arrow 2 indicates the approximate location of the cut made to remove the radical.

In one embodiment of the invention, meristem tissue is used as the starting, or explant, material. To obtain this material, seeds are surface sterilized, and germinated by culturing on an appropriate medium, preferably in the dark, for a period of from 0-10 days, under conditions appropriate for the particular species and cultivar. As shown in FIG. 1, mesocotyl sections are obtained by removing the upper portion of the coleoptile and roots around the crown region from the germinating seedling. It is important when excising the mesocotyl explant to leave a whole piece of the scutellum attached to the explant, in order to avoid damaging the meristem tissue of the scutellar node. These mesocotyl explants include several different and distinct primary meristems, such as a scutellar node, a coleoptile node, a first leaf bud and possibly several leaf nodes, and an apical meristem. The mesocotyl explant thus comprises an apical meristem and axillary meristems, including the scutellar node meristem and portions of the primordial sheathing leaves. In an alternative embodiment of this explant, the root tissue around the crown region is left intact, resulting in a partial seedling explant containing the meristems described for the mesocotyl explant.

Alternatively, mature embryos of wheat are used as the explant. To obtain mature embryos, mature seeds are soaked in sterile distilled water and then surface sterilized. Mature embryos attached to a portion of the whole scutellum are isolated. These mature embryo explants contain the same meristems as the mesocotyl explants described above.

In still another embodiment, wheat immature embryos from immature seeds are used. To obtain these explants, wheat spikes are harvested about 14 days after anthesis. Caryopses are surface sterilized, and pericarps in one side of the embryos are opened with a sterile scalpel. The immature embryos are then pressed out of the pericarps by pressing in the embryo region with the scalpel blade tip. This immature embryo explant comprises an apical meristem and axillary meristems, including the scutellar node meristem.

The present invention is genotype independent, as multiple genotypes were successfully utilized in wheat. Five genotypes were tested including Bobwhite, three spring elite lines (252BW012, N92-0248, Autry525), and a winter elite line (X-90-37A). The spring elite lines were selected as representative highly regenerable (252BW012), moderately regenerable (N92-0248), and low regenerability (Autry525) lines, based on a previous study of the regenerability of 41 elite lines. The regenerability of the winter elite line was unknown. Once the regenerable explant tissue is isolated, the tissue is cultured on multiple shoot inducing media, which comprises a basal plant tissue culture media supplemented with a cytokinin and an auxin. There are a variety of basal plant tissue culture media commonly used in the art, typically made up of components that may include macronutrients, micronutrients, vitamins, supplements, carbohydrates, growth regulators, and gelling agents. Those skilled in the art are aware that the combinations, proportions and concentrations of the particular components in the culture media are variable for different plant species, and even for different cultivars of the same species. The culture media can be manipulated by skilled practitioners to induce a variety of tissue responses. Examples of suitable basal plant tissue culture media include MS based media (Murashige and Skoog, *Physiol. Plant,* 15:473-497, 1962), N6 based media (Chu, *Proc. Symp. Plant Tissue Culture*. Peking: Science Press. Pp.43-50, 1978), Gamborg's media (Gamborg et al., *Exp. Cell Res.,* 50:151, 1968), McCown's Woody Plant media (McCown and Lloyd, *HortScience,* 16:453, 1981), Nitsch and Nitsch media (Nitsch and Nitsch, *Science,* 163:85-87, 1969), and Schenk and Hildebrandt media (Schenk and Hildebrandt, *Can.J. Bot.* 50:199-204, 1972). Typically, supplements such as nutrients, growth regulators, and other additives are optimized to achieve the desired response. It is an object of the present invention to provide a multiple shoot inducing media to achieve a multiple shooting response from the explants.

The preferred multiple shoot inducing media of the present invention is supplemented with additional nutrients and/or growth regulators including but not limited to cytokinins, auxins, and abscisic acid (ABA). A number of cytokinins are available to the skilled artisan, and include zeatin, 2-iP (N6-(2-isopentyl)adenine), dihydrozeatin, kinetin, BAP or BA (6-benzylaminopurine), PBA or SD 8339 ((6-benzylamino)-

9-(2-tetrahydropyranyl)-9H-purine), thidiazuron (TDZ), 2Cl-4PU or CPPU (N-2-chloro-4-pyridyl)-N"-phenylurea), or 2,6Cl-4PU (N-(2,6-dichloro-4-pyridyl)-N"-phenylurea). Similarly, a number of auxins are available including IAA (3-indole-acetic acid), 2,4-D (2,4-dichlorophenoxyacetic acid), IBA (3-indolebutyric acid), NAA (1-naphthalene acetic acid), NOA (2-naphthyloxyacetic acid), MCPA (2-methyl-4-chlorphenoxyacetic acid), 2,4,5-T (2,4,5-trichlorophenoxyacetic acid), dicamba (3,6-dichloroanisic acid), and picloram (4-amino-3,5,6-trichloropicolinic acid). Preferred growth regulators for use with the basal plant tissue culture media in the present invention include a combination comprising cytokinin, or a compound homologous to cytokinin, and auxin. The preferred concentration range of cytokinin is about 0.01-20 mg/L; or about 0.5-10 mg/L; or about 1-5 mg/L. The preferred concentration range of auxin is about 0.025-5.0 mg/L; or about 0.05-2.0 mg/L. The preferred growth regulator combination includes TDZ, BAP, kinetin, or zeatin as the cytokinin, and 2,4-D or picloram as the auxin. Table 1 summarizes the multiple shoot inducing media compositions for use in the present invention.

TABLE 1

Important Multiple Shoot Inducing Media Compositions

| Medium name | Medium composition |
|---|---|
| MMSOCY | 4.3 g/L Gibco MS (500-1117E11*) + 1.95 g/L MES + 2 mL/L MMS vitamin + 40 g/L maltose (M-5885**) + 0.1 g/L casein hydrolysate (C-9386**) + 7 g/L Phytagar (670-0675-IP*); pH: 5.8 with KOH |
| MSIM12 | MMSOCY + 100 mg/L ascorbic acid + 2.5 mg/L TDZ + 0.5 mg/L 2,4-D |
| MSIM13 | MMSOCY + 100 mg/L ascorbic acid + 2.5 mg/L TDZ + 0.5 mg/L 2,4-D + 0.26 mg/L ABA |
| MSIM14 | MMSOCY + 100 mg/L ascorbic acid + 4 mg/L TDZ + 1 mg/L 2,4-D |
| MSIM15 | MMSOCY + 100 mg/L ascorbic acid + 4 mg/L TDZ + 1 mg/L 2,4-D + 0.26 mg/L ABA |
| MSIM16 | MMSOCY + 100 mg/L ascorbic acid + 7.5 mg/L TDZ + 2 mg/L 2,4-D |
| MSIM15P | MMSOCY + 100 mg/l ascorbic acid + 4 mg/L TDZ + 1 mg/L picloram + 0.26 mg/L ABA |
| MSIM15B | MMSOCY + 100 mg/L ascorbic acid + 4 mg/L BA + 1 mg/L 2,4-D |
| MSIM12B | MMSOCY + 100 mg/L ascorbic acid + 2.5 mg/L BA + 0.5 mg/L 2,4-D |

*Catalog number from Gibco-BRL (Grand Island, NY)
**Catalog number from Sigma Chemical Co. (St. Louis. MO)

Any culture conditions suitable for plant growth and development can be used and optimized for the particular crop and cultivar. Those skilled in the art are aware of the environmental conditions required for growth and development of plants. The present invention utilizes a temperature range of about 22° C.-32° C., and standard 16-hour photoperiod. The usual temperature for wheat is 25° C. The environmental culture conditions described herein are not limiting, and skilled artisans will readily be able to manipulate the conditions to optimize plant growth and development.

In a particular embodiment of the invention, the regenerable cells are transformed prior to or during the process of regeneration, thus giving rise to whole, transformed, fertile mature plants. Three developmental stages in the regeneration process are most suitable for transformation. The three stages are defined as 1) early meristem enlargement (EME) when the meristem surface is significantly enlarged without the emergence of secondary multiple shoot meristems (identified under dissecting microscope); 2) late meristem enlargement (LME) when meristem surface is significantly enlarged and the initiation of secondary multiple shoot meristems (identified under dissecting microscope) has begun; and 3) multiple bud formation (MBF) when multiple bud formation including the true leaf has emerged on the enlarged meristems (visually identified). For the purpose of the present invention, transformed refers to the introduction and stable integration of exogenous DNA into the plant cell by any means, resulting in genetic modification. The exogenous DNA may be integrated into the genome, or alternatively into the plastid genome. Methods of introducing exogenous DNA into the genome of plant cells are well known in the art. (Gordon-Kamm et al., Plant Cell, 2, 603-618, 1990; Vasil et al., Bio/Technlogy, 10, 677-674, 1992). Likewise, methods of introducing foreign DNA into the plastid genome are known in the art (Svab et al., Proc. Natl. Acad. Sci. USA, 87, 8526-8530, 1990).

To initiate a transformation process in accordance with the present invention, it is first necessary to construct a recombinant nucleic acid vector. Means for preparing plasmids or vectors containing the desired genetic components are well known in the art. Vectors used to transform plants and methods of making those vectors are described in the literature. Vectors typically consist of a number of genetic components, including but not limited to, regulatory elements such as promoters, leaders, introns, and terminator sequences.

Transcription of DNA into mRNA is regulated by a region of DNA usually referred to as the "promoter." A number of promoters that are active in plant cells have been described in the literature. Such promoters would include, but are not limited to, the nopaline synthase (NOS) and octopine synthase (OCS) promoters, which are carried on tumor-inducing plasmids of *Agrobacterium tumefaciens*; the caulimovirus promoters such as the cauliflower mosaic virus (CaMV) 19S and 35S promoters and the figwort mosaic virus (FMV) 35S promoter; the enhanced CaMV35S promoter (e35S); and the light-inducible promoter from the small subunit of ribulose bisphosphate carboxylase (ssRUBISCO, a very abundant plant polypeptide). All of these promoters have been used to create various types of DNA constructs that have been expressed in plants. See, for example PCT publication WO 84/02913.

Promoter hybrids can also be constructed to enhance transcriptional activity (see U.S. Pat. No. 5,106,739) or to combine desired transcriptional activity, inducibility, and tissue or developmental specificity. Promoters that function in plants are promoters that are inducible, viral, synthetic, constitutive as described (Poszkowski et al, *EMBO J.*, 3:2719, 1989; Odell et al., *Nature*, 313:810, 1985), and temporally regulated, spatially regulated, and spatio-temporally regulated (Chau et al., *Science*, 244:174-181, 1989). Other promoters that are tissue-enhanced, tissue-specific, or developmentally regulated are also known in the art and envisioned to have utility in the practice of this invention. Promoters may be obtained from a variety of sources such as plants and plant DNA viruses. As described below, it is preferred that the particular promoter selected should be capable of causing sufficient expression to result in the production of an effective amount of the gene product of interest.

The promoters used in the DNA constructs (i.e., chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al. (*Science*, 236:1299, 1987).

The mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes (see, for example, U. S. Pat. No. 5,362,865). Other genetic components that serve to enhance expression or affect transcription or translational of a gene are also envisioned as genetic components. The 3' non-translated region of the chimeric constructs should contain a transcriptional terminator, or an element having equivalent function, and a polyadenylation signal, which functions in plants to cause the addition of polyadenylated nucleotides to the 3' end of the RNA. Examples of suitable 3' regions are (1) the 3' transcribed, non-translated regions containing the polyadenylation signal of Agrobacterium tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3" region is that from the ssRUBISCO E9 gene from pea (European Patent Application 385,962, herein incorporated by reference in its entirety).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

Recombinant nucleic acid vectors may also contain a selectable, screenable, or scoreable marker gene. These genetic components are also referred to herein as functional genetic components, as they produce a product that serves a function in the identification of a transformed plant, or a product of desired utility. The DNA that serves as a selection device functions in a regenerable plant tissue to produce a compound that would confer upon the plant tissue resistance to an otherwise toxic compound. Genes of interest for use as a selectable, screenable, or scorable marker would include, but are not limited to, β-glucuronidase (GUS), green fluorescent protein (GFP), luciferase (LUX), antibiotic or herbicide tolerance genes. Examples of transposons and associated antibiotic resistance genes include the transposons Tns (bla), Tn5 (npt II), Tn7 (dhfr); penicillins; kanamycin (and neomycin, G418, bleomycin); methotrexate (and trimethoprim); chloramphenicol; and tetracycline. Characteristics useful for selectable markers in plants have been outlined in a report on the use of microorganisms (Advisory Committee on Novel Foods and Processes, July 1994). These include i) stringent selection with minimum number of nontransformed tissues; ii) large numbers of independent transformation events with no significant interference with the regeneration; iii) application to a large number of species; and iv) availability of an assay to score the tissues for presence of the marker.

As mentioned, several antibiotic resistance markers satisfy these criteria, including those resistant to kanamycin (nptII), hygromycin B (aph IV), and gentamycin (aac3 and aac C4).

Particularly preferred selectable marker genes for use in the present invention would include genes that confer resistance to compounds such as antibiotics like kanamycin (Dekeyser et al, *Plant Physiol.*, 90:217-223, 1989), and herbicides like glyphosate (Della-Cioppa et al., *Bio/Technologqy*, 5:579-584, 1987). Other selection devices can also be implemented and are within the scope of the present invention.

The present invention can be used with any suitable plant transformation plasmid or vector, containing a selectable or screenable marker or not, and associated regulatory elements as described, along with one or more nucleic acids expressed in a manner sufficient to confer a particular desirable trait. Examples of suitable structural genes of interest envisioned by the present invention would include, but are not limited to, genes for insect or pest tolerance; herbicide tolerance; genes for quality improvements such as yield, nutritional enhancements, environmental or stress tolerances; or any desirable changes in plant physiology, growth, development, morphology, or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech Gen. Engin. Rev.*, 9:207-227, 1991). The RNA could also be a catalytic RNA molecule (i.e., a ribozyme) engineered to cleave a desired endogenous mRNA product (see, for example, Gibson and Shillitoe, *Mol Biotech.*, 7:125-137, 1997). Thus, any gene that produces a protein or mRNA that expresses a phenotype or morphology change of interest is useful for the practice of the present invention.

Exemplary nucleic acids that may be introduced by the methods encompassed by the present invention include, for example, DNA sequences or genes from another species, or even genes or sequences that originate with or are present in the same species but are incorporated into recipient cells by genetic engineering methods rather than classical reproduction or breeding techniques. However, the term exogenous is also intended to refer to genes that are not normally present in the cell being transformed or to genes that are not present in the form, structure, etc., as found in the transforming DNA segment or to genes that are normally present but a different expression is desirable. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible selectable or screenable marker genes, regulatory elements, and other sequences of interest will be apparent to those of skill in the art. Therefore, the foregoing discussion is intended to be exemplary rather than exhaustive.

The invention disclosed herein relies on introducing the recombinant nucleic acid vector into meristematic tissue by any suitable means. Meristematic tissue does not require a de-differentiation process in order to regenerate transgenic plants; these meristematic cells need only have growth redirected in order to produce whole transgenic plants (Sauter et al., Plant J. 7(4):623-632, 1995). Others have disclosed methods whereby primary meristems are used as target tissue for the introduction of recombinant nucleic acid vectors, and subsequently, the tissue is redirected to produce whole transgenic plants. Typically, the meristem tissue is freshly isolated from a seed or seedling and is transformed thereafter with or without a preculture period. Subsequently, the tissue is redirected via media manipulation, to regenerate whole transgenic plants. In some cases, the explant material is manipulated to produce multiple shoots after the introduction of a recombinant nucleic acid vector to increase the efficiency of the method.

The method of this invention thus comprises, however, the use of an explant comprising one or more primary meristems that is cultured in a multiple meristem inducing media to achieve a multiple shooting response prior to transformation. Thus, the primary meristems give rise to multiple secondary buds, in some cases upwards of one hundred secondary buds per primary meristem. These secondary buds then are used as the target for the transformation process, thus increasing the quantity of target cells per explant. As a result, instead of requiring a greater number of explants in order to increase the output of the transformation process, this invention allows for an increase in the quantity of target tissue of each explant by manipulating the explant to produce multiple secondary buds from each primary meristem prior to the introduction of the recombinant nucleic acid vector. The method of this invention thus allows for an increased output without significantly increasing the amount of labor or plant tissue input.

The present invention provides a reproducible, efficient method of obtaining transformed plants that is genotype independent and is labor-saving and cost-effective. In addition, the method is capable of producing plants faster than conventional methods. Plants can be recovered as soon as 8-13 weeks from initiation of the method. The invention is further described by the following non-limiting examples.

These examples may be better understood by referring to FIG. 1, which is a longitudinal section showing the mesocotyl explant, one of the preferred explants of the present invention. Arrow 1 indicates the approximate location of the cut made to remove the upper portion of the coleoptile. Arrow 2 indicates the approximate location of the cut made to remove the lower portion of the coleoptile. In this figure, the apical meristem, coleoptile bud, and scutellar node are shown. The scutellar node contributes a large primary meristem, from which a large number of secondary meristems can be produced when cultured according to this invention. It is thus important to include this primary meristem in the tissue of the explant for the best regeneration response according to this invention. The scutellum, a portion of which is pictured in FIG. 1, can be cut along the axes indicated by arrows 1 and 2, but this portion of the scutellum should be left intact, so as not to damage the meristem tissue in this region of the explant. An alternative embodiment of the mesocotyl explant, termed a partial seedling, is identical to the mesocotyl explant, except the cut along axis 2 is omitted. Thus, the resulting partial seedling explant retains the roots around the crown region.

EXAMPLE 1

Explant Preparation

A. Wheat mesocotyl explant: Mature wheat seeds were surface sterilized first in 70% ethanol for 1 min. and then soaked in 20% CLOROX® (5.25% sodium hypochlorite) and shaken at 250 rpm for 20 min. The seeds were then rinsed five times with sterile distilled water and then placed in 100×25 mm petri dishes containing a sterile piece of felt and ~15 mL of double distilled sterile water with 5 µM BA for germination. The seeds were cultured for 1 day in darkness at ~24° C. Mesocotyl sections about 2-3 mm in length were then excised by removing the upper portion of the coleoptile, approximately 1-1.5 mm in length, and root tissue around the crown region. These mesocotyl explants contain at least several different and distinct meristems, such as a scutellar node, a coleoptile node, a first leaf bud and possibly several leaf nodes, and an apical meristem. This mesocotyl explant thus comprises an apical meristem and several axillary meristems, including the scutellar node meristem. It is important when excising the mesocotyl explant to leave a whole piece of the scutellum attached to the explant, because the scutellar node meristem contributes a large primary meristem from which upwards of 100 buds can be produced via the method of the present invention, relative to the small primary meristems contributed by the other meristems from which a smaller number of buds can be produced. It is also important that the explants have all of the described meristems intact after excision, in order to maximize multiple bud response in culture.

B. Wheat mature embryo explant: Mature wheat seeds were soaked in sterile distilled water in a flask for 24 hr., then surface sterilized as described above, and then mature embryos were excised, which contain the same meristems described above.

C. Wheat immature embryo explant: Wheat spikes were harvested about 14 days after anthesis. Caryopses were surface sterilized by soaking first in 70% ethanol for 1 min and then in 10% CLOROX® with ten drops of TWEEN 20 per 1 L for 15 min, followed by four rinses in sterile distilled water. Pericarps in one side of the embryos were opened with a sterile scalpel blade, and immature embryos were pressed out of the pericarps by pressing in the embryo region with the scalpel blade tip.

EXAMPLE 2

Regeneration Conditions

Wheat explants such as mesocotyl sections from seedlings, mature embryos from mature seeds, and immature embryos from immature seeds were cultured on multiple shoot inducing media comprising combinations of cytokinins, auxins and abscisic acid (ABA). The most preferred cytokinin was thidiazuron (TDZ) at 1 to 10 mg/L. The particular auxins used were 2,4-dichlorophenoxyacetic acid (2,4-D) at 0.1 to 1 mg/L and picloram at 0.1 to 1 mg/L. The most preferred media with combinations of cytokinins, auxins and ABA contained TDZ at 1 to 10 mg/L, 2,4-D at 0.1 to 1 mg/L and ABA at 0 to 2.6 mg/L. Another preferred media contained TDZ at 1 to 10 mg/L, picloram at 0.1 to 1 mg/L and ABA at 0 to 2.6 mg/L. The protocols used MS basal medium supplemented with the combination of cytokinins, auxins and ABA as described above, ascorbic acid at 100 mg/L, 2-[N-Morpholino]ethanesulfonic acid (MES) at 1.95 g/L, casein hydrolysate at 100 mg/L, and maltose at 40 g/L. More generally, a cytokinin such as kinetin, BAP and zeatin at 0.5 to 10 mg/L combined with 2,4-D at 0.05 to 1 mg/L also are used for meristem explant culture. The particular media compositions used for this invention are described in detail in Table 1. The mesocotyl explants were placed on media with the acropetal end up, and mature and immature embryo explants were placed on media with the scutellum-side up. All cultures were placed under 16 h photoperiod at about 25° C.

For the first three weeks, the explants were usually trimmed, by removing the top portion of coleoptile 3-5 mm above the crown region for wheat, every 3 to 5 days to inhibit dominant growth. This dominant growth response varied depending on genotype and seed source, and care was taken in all cases not to overtrim the explants resulting in damage to the meristem tissue.

Usually three to five weeks after the induction stage culture described above, multiple bud clumps were divided and transferred to a shoot elongation medium, and cultured under 16 h photoperiod at about 25° C. for 3 to 4 weeks. The shoot elongation medium comprised MS basal medium supplemented with ascorbic acid at 100 mg/L, 2-[N-Morpholino] ethanesulfonic acid (MES) at 1.95 g/L, casein hydrolysate at 100 mg/L, maltose at 40 g/L, and Schweizer-Hall® gelling agent at 2 g/L. The elongated shoots were transferred to a rooting medium, comprising MS basal medium supplemented with IBA at 1 mg/L, ascorbic acid at 100 mg/L, 2-[N-Morpholino] ethanesulfonic acid (MES) at 1.95 g/L, casein hydrolysate at 100 mg/L, maltose at 40 g/L, and Schweizer-Hall® gelling agent at 2 g/L, for 3 to 4 weeks, after which sufficient roots had formed to transfer the shoots to soil.

EXAMPLE 3

Multiple Shoot Induction in Wheat

Multiple shoot induction using mesocotyl explant Scutellar node primary meristems of mesocotyl explants from all cultures started to multiply 10 to 20 days after culture initiation on various multiple meristem inducing media (Tables 1, 2, 3, 4, 5, 7). The primary meristems were enlarged and then reorganized by initiating multiple secondary buds from a single primary meristem. After 2-3 weeks, the other primary meristems such as the coleoptile node, leaf node and apical meristems started the same process that the scutellar node meristems went through, initiating multiple secondary buds. This multiple meristem response was dependent upon specific media compositions as described in more detail below. The whole process from meristem enlargement stage to multiple bud cluster formation occurred without intervening callus formation on the explants. For all cultures, multiple buds or shoots were visible, emerging from the pre-existing primary meristems on the explants. If the pre-existing primary meristems were completely cut off from the explants, there was no culture response, indicating the importance of keeping the explant intact during the induction stage.

Four different cytokinins, not in combination with auxin, were tested for their ability to induce multiple shoot induction on wheat mesocotyl explants: BA, kinetin, zeatin and TDZ. Among the four cytokinins tested, TDZ generated the highest percentage of meristems producing one shoot (Table 2). However, none of the explants produced multiple buds or shoots from a single primary meristem for any of the four cytokinins tested. There was little difference between the 16-hour photoperiod and continuous dark lighting conditions on multiple shoot induction except with the cytokinin zeatin, where darkness for the first two weeks produced the best response (Table 2).

TABLE 2

Effects of cytokinins and lighting conditions on multiple shoot production 32 days after culture using mesocotyl wheat explants.**

| Cytokinin (5 mg/L)/lighting condition | No. of explants | % of explants producing 2-5 shoots (each from a single primary meristem) | % of explants producing multiple shoots from a single primary meristem |
|---|---|---|---|
| BA/(L) | 20 | 10.0 | 0 |
| BA/(D) | 20 | 15.0 | 0 |
| Kinetin/(L) | 20 | 20.0 | 0 |
| Kinetin/(D) | 21 | 23.8 | 0 |
| Zeatin/(L) | 20 | 20.0 | 0 |
| Zeatin/(D) | 20 | 45.0 | 0 |
| TDZ/(L) | 20 | 80.0 | 0 |
| TDZ/(D) | 21 | 76.2 | 0 |

**(L) = incubation at 16 h photoperiod for four weeks
(D) = incubation at continuous dark for the first two weeks, then under light (16/8) for the additional two weeks Different combinations of a cytokinin and an auxin were examined to determine the effect on multiple bud induction from a single primary meristem. Four different media, MSIM12, MSIM13, MSIM15 and MSIM16 (Table 1), were tested along with a control containing TDZ alone. The media tested contained different concentrations of TDZ, 2,4-D and ABA. An average of 88.4 to 97.9% of explants responded with multiple bud formation from a single primary meristem, and 73.1 to 95.5% of explants produced 20-80 buds from each primary meristem for the four media tested, whereas TDZ alone did not produce a similar response (Table 3). The medium MSIM15 generated the best response, both in terms of the percentage of explants responding, and the percentage of explants producing multiple (20-80) buds per primary meristem. This indicates that the combination of the cytokinin TDZ with an auxin was most effective for multiple bud formation from a single primary meristem within the time period tested.

TABLE 3

Effects of TDZ alone and combinations of TDZ (cytokinin) with 2,4-D (auxin) on multiple bud induction 4 weeks after culture initiation using wheat mesocotyl explants

| Medium | No. of explants | % explants responding | % explants producing 20-80 buds/primary meristem | No. primary meristems produced/ explant |
|---|---|---|---|---|
| TDZ alone | 41 | 0 | 0 | 2-5 |
| MSIM12 | 47 | 97.9 | 87.2 | 1-4 |
| MSIM13 | 22 | 90.9 | 86.4 | 1-4 |
| MSIM15 | 22 | 95.5 | 95.5 | 1-4 |
| MSIM16 | 26 | 88.4 | 73.1 | 1-3 |

TDZ was compared to BA in terms of the ability to induce multiple bud formation from the mesocotyl explants. Two different combinations were tested, with either BA or TDZ as the cytokinin. In both cases, the media containing TDZ induced a high percentage of explants exhibiting multiple bud response, whereas the media containing BA failed to induce any explants showing the multiple bud response (Table 4). This clearly indicated that TDZ in combination with auxin is beneficial for inducing the desired multiple bud response in wheat mesocotyl explants.

TABLE 4

Effects of different cytokinins (BA vs. TDZ) on multiple bud formation using mesocotyl explants about 4 weeks after culture initiation in wheat.**

| Medium | No. of explants | % explants responding | % explants producing 20-80 buds from each primary meristem | Mean primary meristems produced/explant |
|---|---|---|---|---|
| MSIM15 | 50 | 100 | 98.1 | 2.8 (2-7) |
| MSIM15B | 40 | 65.0 | 0 | 0.7 (0-2) |
| MSIM12 | 47 | 97.9 | 87.2 | 2.5 (1-4) |
| MSIM12B | 32 | 68.8 | 0 | 0.9 (0-2) |

**Media MSIM15, MSIM15B, MSIM12 and MSIM12B were formulated based on the same MS basal medium, but contained different cytokinins, 4 mg/L TDZ + 1 mg/L 2,4-D, 4 mg/L BA + 1 mg/L 2,4-D, 2.5 mg/L TDZ + 0.5 mg/L 2,4-D and 2.5 mg/L BA + 0.5 mg/L 2,4-D, respectively (see Table 1).

Growth conditions. Table 5 shows the effect of lighting conditions on the production of multiple buds. There is a strong trend showing a better response when cultured in the light, but multiple buds were produced under dark culture conditions as well. This again emphasizes the significance of the media composition in producing the desired multiple budding result.

TABLE 5

Effects of lighting conditions on multiple meristem formation using medium with different combinations of growth regulators, using wheat mesocotyl explants about 5 weeks after culture initiation**

| Medium/ lighting condition | No. of explants | % explants responding | % explants producing 20-80 buds/primary meristem | Mean # meristems produced/ explant | Mean #buds produced/ explant |
|---|---|---|---|---|---|
| MSIM12/L | 12 | 100 | 100 | 4.0 (1-7) | 93 |
| MSIM12/D | 11 | 81.8 | 81.8 | 2.5 (0-5) | 73 |
| MSIM13/L | 12 | 83.3 | 83.3 | 2.4 (0-4) | 67 |
| MSIM13/D | 12 | 83.3 | 75.0 | 2.5 (0-5) | 63 |
| MSIM15/L | 44 | 100 | 97.7 | 3.0 (1-7) | 95 |
| MSIM15/D | 50 | 100 | 98.0 | 3.0 (1-5) | 97 |
| MSIM16/L | 14 | 100 | 78.6 | 3.0 (1-5) | 69 |
| MSIM16/D | 13 | 69.2 | 61.5 | 2.9 (0-8) | 49 |

**Lighting conditions were under 16 h photoperiod for entire culture (L), or under continuous darkness for the first two weeks and 16 h photoperiod for the remainder of culture time (D).

Genotype Independence. Four elite wheat lines, 251BW012, Autry525, N92-0248 (spring lines) and X-90-37A (winter line) were tested to determine genotype-independence using media MSIM15 (comprising 4.0 mg/L TDZ and 1.0 mg/L 2,4-D; see Table 1), with Bobwhite as a control representing standard regenerability. The three spring elite lines, 251BW012, Autry525, N92-0248, were representative "good", "average" and "poor" lines respectively, regarding their regenerability, based on a previous study of 41 spring elite lines. There is no known information regarding the regeneration capacity for the winter elite line. The four elite lines showed multiple bud response in the same range as Bobwhite, indicating that the method of the present invention is genotype independent (Table 6).

TABLE 6

Effects of genotype on multiple bud formation in medium MSIM15 using wheat mesocotyl explants about 4 weeks after culture initiation.

| Genotype | No of explants | % explants responding | % explants producing 20-80 buds/primary meristem | Mean primary meristems produced/explant |
|---|---|---|---|---|
| Bobwhite | 115 | 100 | 98.1 | 2.8 (2-7) |
| 251BW012 | 17 | 100 | 70.6 | 2.4 (1-7) |

TABLE 6-continued

Effects of genotype on multiple bud formation in medium MSIM15 using wheat mesocotyl explants about 4 weeks after culture initiation.

| Genotype | No of explants | % explants responding | % explants producing 20-80 buds/primary meristem | Mean primary meristems produced/explant |
|---|---|---|---|---|
| Autry525 | 19 | 94.7 | 61.1 | 2.3 (1-3) |
| N92-0248 | 11 | 100 | 31.8 | 2.6 (1-4) |
| X-90-37A | 9 | 100 | 38.9 | 2.2 (1-3) |

Testing Different Types of Meristem Explants. Mature and immature embryo explants were compared to mesocotyl explants, in terms of the ability to produce multiple buds from a single primary meristem (Table 7). The results indicate that this regeneration system induces efficient multiple bud formation from a single primary meristem with all types of vegetative meristems including mesocotyl explants, mature embryos and immature embryos, with the response in mesocotyl explants being superior.

TABLE 7

Multiple bud formation using wheat mesocotyl explants (MS), mature embryos (ME) and immature embryos (IE) as starting material, about 4 weeks after initiation.

| Explant/ medium | No. of explants | % explants responding | % explants producing 20-80 buds/primary meristem | Mean primary meristems produced/ explant |
|---|---|---|---|---|
| MS/MSIM15 | 115 | 100 | 98.1 | 2.8 (2-7) |
| ME/MSIM15 | 49 | 100 | 95.9 | 2.9 (1-4) |
| IE/MSIM12 | 24 | 95.8 | 75.0 | 2.0 (1-3) |

Shoot Elongation and Rooting.

Three genotypes were tested to evaluate shoot elongation from the buds induced in the above described multiple shoot induction step. Bobwhite, 251BW012 and Autry525 were chosen as representative standard, good and poor lines respectively, based on a previous study of embryogenic regeneration capacity. The buds were removed from the media containing the growth regulator combination described in the induction stage, after about 3-5 weeks of culture. The explants at this point can be divided into clumps of buds and transferred to media without growth hormones for elongation and rooting. Table 8 shows the relative response for the three genotypes tested after 3-4 weeks of culture on the hormone free media. All of the genotypes produced multiple elongated shoots. Table 9 shows the rooting response of Bobwhite shoots in media to which IBA had been added at a concentration of 1 mg/L. The addition of IBA at 1 mg/L significantly increased the rooting response. After 3 months in the greenhouse, 35 Bobwhite plants and 9 elite plants were recovered. All the plants were healthy and fertile.

TABLE 8

Shoot elongation of different genotypes using wheat mesocotyl explants, after 3-4 weeks of culture on hormone free media.

| Genotype | No. of explants | Mean # of elongated shoots/ explant (1-9 cm in length) |
|---|---|---|
| Bobwhite | 32 | 48.3 |
| 251BW012 | 12 | 20.8 |
| Autry525 | 9 | 25.6 |

TABLE 9

Effect of IBA on root induction using shoots from Bobwhite mesocotyl explants.

| Medium | No. explants | % shoots producing roots |
|---|---|---|
| MS + 1 mg/L IBA | 39 | 92.1 |
| MS | 25 | 53.6 |

EXAMPLE 4

Biolistic Transformation of Wheat

Wheat (cv. Bobwhite) mesocotyl and mature embryo explants were cultured on medium MSIM15 or MSIM12 for wheat for three to four weeks following the regeneration protocols.

Induced wheat primary meristems from three developmental stages were used as targets for transformation by means of the biolistic method. The three stages were defined as 1) early meristem enlargement (EMIE) when the meristem surface was significantly enlarged without the emergence of secondary multiple shoot meristems (identified under dissecting microscope); 2) late meristem enlargement (LME) when meristem surface was significantly enlarged and the initiation of secondary multiple shoot meristems (identified under dissecting microscope) had begun; and 3) multiple bud formation (MBF) when multiple bud formation had emerged on the enlarged meristems (visually identified).

The induced meristem explants from EME, LME and MBF stages for wheat were isolated and incubated on the solid osmotic media, medium CM4C Raff/Mann0.25 for wheat in the dark for 4 to 6 h, respectively. The medium CM4C Raff/Mann0.25 contained MS basal medium+40 g/L maltose, 74.31 g/L raffinose, 22.78 g/L mannitol, 0.5 g/L glutamine, 0.75 g/L magnesium chloride, 1.95 g/L MES, 0.1 g/L casein hydrolysate, 0.5 mg/L 2,4-D, 2.2 mg/L picloram, 100 mg/L ascorbic acid, and 2 g/L phytagel.

Figure 2:
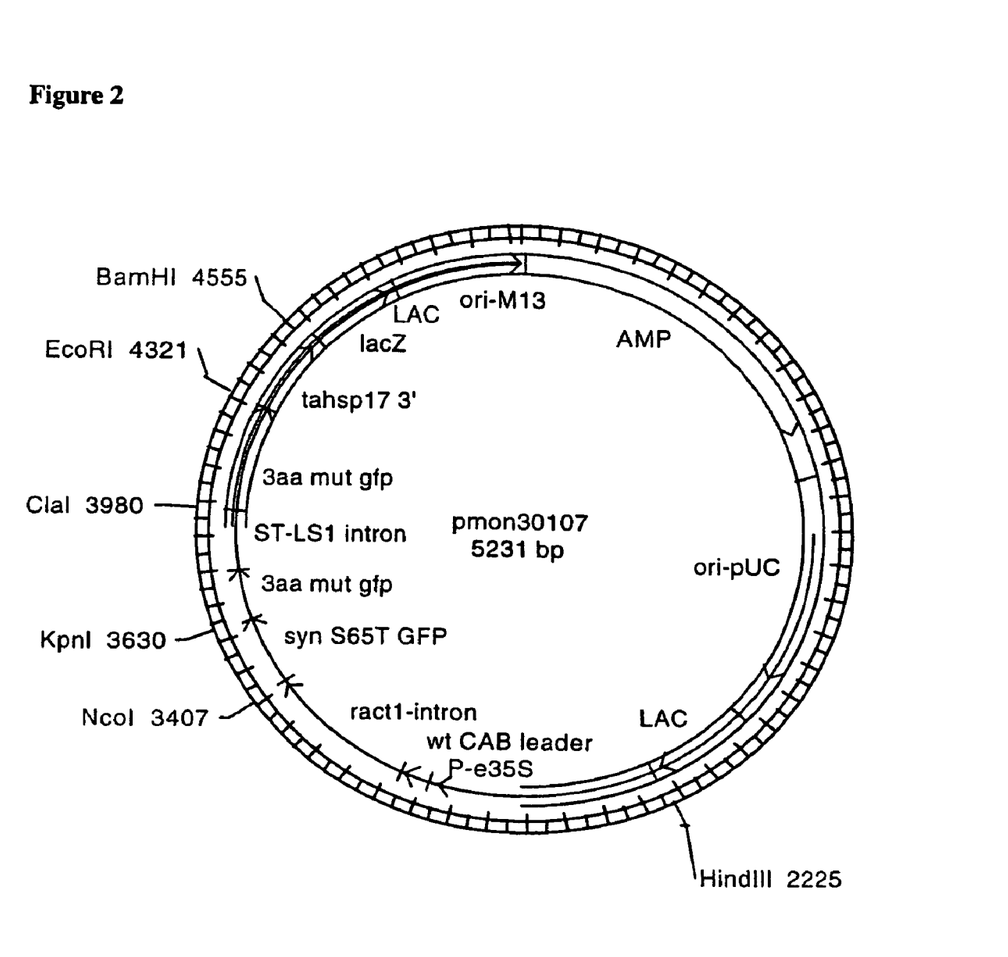
FIG. 2 is a plasmid map of pMON30107.
Figure 3:
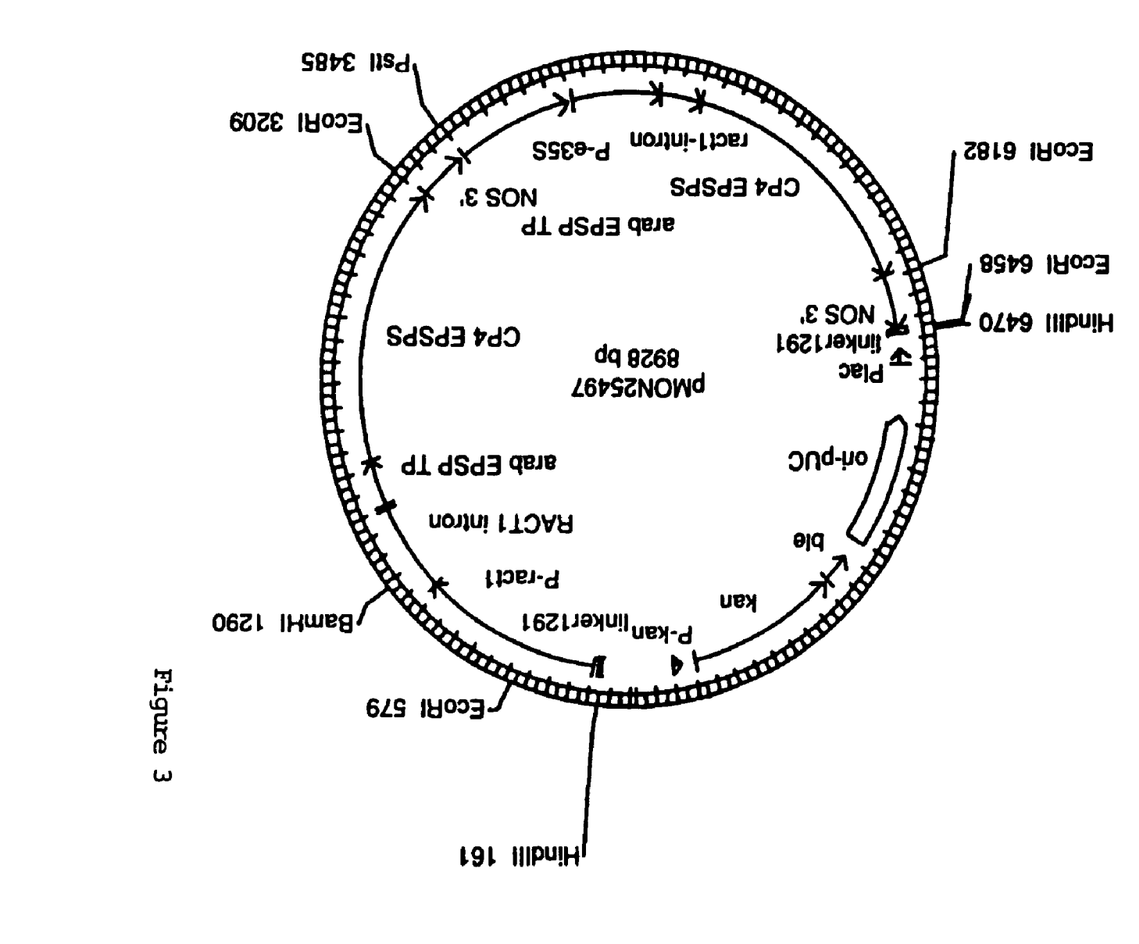
FIG. 3 is a plasmid map of pMON25497.
Figure 4:
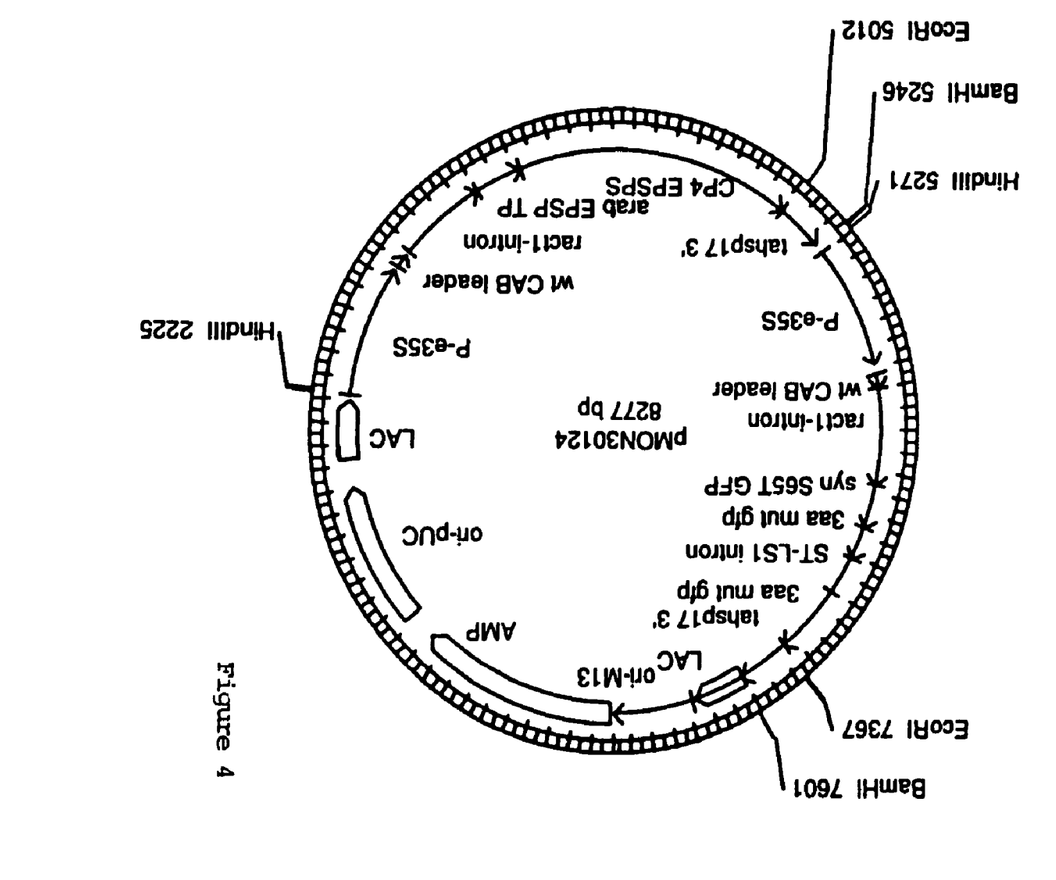
FIG. 4 is a plasmid map of pMON30124.

The plasmids pMON30107 (FIG. 2), pMON25497 (FIG. 3), and pMON30124 (FIG. 4) were used for transformation. The plasmid pMON30107 contains a gfp gene driven by an enhanced CaMV 35S promoter. The plasmid pMON25497 contains double cp4 EPSPs synthase genes, which confer resistance to glyphosate, one driven by an enhanced CaMV 35S promoter and the other one driven by a rice actin 1 (Ract 1) promoter. The plasmid pMON30124 contains a gfp and a cp4 EPSPs gene each driven by an enhanced CaMV 35S promoter.

Prior to bombardment, 125 mg of M10 tungsten was suspended in 2.5 mL of absolute ethanol and stored at −20° C. until use. Five hundred microliters of the tungsten suspension was aliquoted into a sterile 1.5-mL microcentrifuge tube, washed in sterile distilled water, and resuspended in 0.25 mL sterile 50% glycerol. The microcentrifuge tube was sonicated to disperse particles thoroughly immediately before beginning the DNA precipitation. The mixture used for bombardment was prepared as follows: 12.5 µL of the sonicated particle suspension was mixed with 2.5 µg of DNA of interest followed by addition of 17.5 µL of a premix containing 2.5 M $CaCl_2$ and 0.1 M spermidine in a ratio of 5 to 2. After precipitating for 20 min at room temperature, 12.5 µL of the supernatant was discarded. For each bombardment, 2.5 µL of the resulting mixture was used.

Approximately 20 to 30 induced meristem explants were placed in the center of a 15×100 mm Petri dish containing medium CM4C Raff/Mann0.25 for wheat and medium 15 AA.Osm.2,4-D for corn. After 4-6 hr in the osmotic treatment, the induced meristem explants were then bombarded using the plasmid pMON30124, or alternatively, a 1:1 mixture of the plasmids pMON30107 and pMON25497 using the gunpowder particle bombardment device (Biolistic™ Particle Delivery System, Model PDS-1000). Each plate was bombarded twice under vacuum (27-28 mmHg). The distance from the stopping plate to the target was 13 cm. About 24 h after bombardment, the meristems were transferred to the medium MSIM12 or MSIM15 without selection, and cultured under 16 h photoperiod for 1 day, and then transferred to the same medium, but containing 0.02 mM glyphosate and cultured under similar conditions until glyphosate resistant shoots were generated. The resistant shoots were transferred to a MS medium containing 1 mg/L IBA with 0.005 mM glyphosate, or MS medium containing 1 mg/L IBA with no selection for 4 to 5 weeks for rooting.

Southern Analysis

Genomic DNA was isolated from leaf tissues of glyphosate resistant plants following the method of Shure et al. (Cell, 35:225-233, 1983). Fifteen µg of wheat total genomic DNA was digested with restriction endonuclease Bgl II and fractionated on a 0.8% agarose gel. The DNA was transferred to Hybond N membrane according to standard procedures (Sambrook et al., *Molecular Cloning: A Laboratory Manual*, Second Edition, Cold Spring Harbor Laboratory Press, Cold Spring Harbor, N.Y., 1989). Probes used for detecting cp4 gene for hybridization were made from 799 bp cp4 fragment from plasmid pMON25497 and $_{32}$P-labeled. After hybridization, the membrane was exposed to X-ray film (BioMax, Kodak) for 3 days at −80° C.

For wheat, 84% to 100% of explants transiently expressed GFP at a high level (too many GFP positive spots to count on each induced meristem) (Table 10). There was no significant difference of GFP transient expression between the induced meristems at EME and LME or between precultured and non-precultured induced meristems (Table 10). However, stable CP4 expression of transformed shoots or buds and plants increased up to 5.4-fold and 10-fold, respectively, when using the induced meristem at LME stage and preculture, compared with the other three treatments (Table 11). Transient GFP expression and stable CP4 expression were also compared with co-bombardment using plasmids pMON30107 and pMON25497, and bombardment using plasmid pMON30124 across the induced meristems at EME and LME stages. Seventy-four to 84% of explants transiently expressed GFP at high level, and no significant difference of the expression among the four treatments (Table 12). The combination of the induced meristems at LME stage and bombardment using plasmid pMON30124 generated the highest frequency (33.3%) of explants producing glyphosate resistant plants compared with the other three treatments (Table 13).

TABLE 10

Transient GFP expression 1 day after co-bombardment with pMON30107 (gfp) and pMON25497 (cp4) in wheat

| Treatment (stage/pre-culture) | No. of explants | % of explants expressing GFP | | |
|---|---|---|---|---|
| | | high level$^x$ | low level$^y$ | total |
| EME/pre-culture | 29 | 89.7 | 10.3 | 100 |
| EME/no pre-culture | 25 | 84.0 | 16.0 | 100 |
| LME/pre-culture | 23 | 100 | | 100 |
| LME/no pre-culture | 22 | 100 | | 100 |

$^x$Too many to count GEP positive spots/explant
$^y$GFP spots < 100/explant

TABLE 11

Stable CP4 expression in wheat.

| Treatment[x] (stage/pre-culture) | % of explants producing glyphosate resistant shoots or buds[y] | % of explants producing glyphosate resistant plants[z] |
|---|---|---|
| EME/pre-culture | 24 1 | 3.5 |
| EME/no pre-culture | 12 0 | 0 |
| LME/pre-culture | 65.2 | 34.7 |
| LME/no pre-culture | 40.9 | 4.5 |

[x]the same experiment as described on Table 10
[y]data was collected 47 days after bombardment
[z]data was collected about 3 months after bombardment

TABLE 12

Transient GFP expression 1 day after co-bombardment with pMON30107 (gfp) and pMON25497 (cp4), and bombarded with pMON30124 containing both gfp and cp4 in wheat.

| Treatment (stage/pre-culture) | No. of explants | % of explants expressing GFP | | |
|---|---|---|---|---|
| | | high level[x] | low level[y] | total |
| EME/co-bombardment | 16 | 81.2 | 18.7 | 100 |
| EME/bombardment | 47 | 74.5 | 25.5 | 100 |
| LME/co-bombardment | 17 | 82.4 | 17.6 | 100 |
| LME/bombardment | 50 | 84.0 | 16.0 | 100 |

[x]Too many to count GFP positive spots/explant
[y]GFP spots <100/explant

TABLE 13

Stable CP4 expression in wheat.

| Treatment | No. of explants | % of explants producing glyphosate resistant plant[x] |
|---|---|---|
| EME/co-bombardment | 16 | 12.5 |
| EME/bombardment | 19 | 10.5 |
| LME/co-bombardment | 17 | 11.8 |
| LME/bombardment | 18 | 33.3 |

[x]data was collected about 4 months after selection

Southern Analysis

Two hybridization fragment signals (~3 kb and up) were detected in 16 out of 17 putative transgenic plants, but not in one putative transgenic plant and the non-transformed Bobwhite control plant. This indicated the chromosomal integration of the cp4 in transgenic plants. The intensities of the bands among sample lanes could have resulted from differences in insert copy number, variation in blotting or a combination of both. The hybridization signal pattern of two fragments in each lane and similar distance between two bands of each sample was observed. It might be explained by assuming that the site of linearization of the plasmid pMON25497 during integration was in the vicinity of the 1.4 kb region.

The invention claimed is:

1. A method of producing multiple transgenic wheat plants from a single explant comprising:
   providing an explant presenting a plurality of meristems;
   culturing said explant on a first media comprising a concentration of thidiazuron and 2,4-D that induces the production of a plurality of buds from at least one of said plurality of meristems;
   introducing exogenous DNA into more than one of said plurality of buds;
   removing said plurality of buds from said first media and transferring said plurality of buds to a second media suitable for induction of elongation of said buds into shoots;
   harvesting and transferring said shoots to a culture medium that promotes root development; and
   culturing said transferred shoots to produce multiple transgenic wheat plants wherein the explant is a wheat mesocotyl explant.

2. The method of claim 1, wherein the concentration of said thidiazuron is between 2.0 mg/L and 7.5 mg/L.

3. The method of claim 1, wherein the concentration of thidiazuron is between 2.0 mg/L and 7.5 mg/L and the concentration of 2,4-D is between 0.5 mg/L and 2.0 mg/L.

4. The method of claim 1, wherein said plurality of meristems contains the scutellar node.

5. The method of claim 1, wherein said exogenous DNA comprises a nucleic acid encoding a protein capable of conferring resistance to a selection agent.

6. The method of claim 5, further comprising a step of selecting for plants containing the protein conferring resistance to a selection agent.

7. The method of claim 1, wherein said exogenous DNA is introduced via biolistic particle bombardment.

8. The method of claim 1, wherein said exogenous DNA is introduced via *Agrobacterium*-mediated transformation.

9. A method of producing multiple transgenic wheat plants from a single explant comprising:
   providing a wheat mesocotyl explant presenting a plurality of meristems;
   culturing said wheat mesocotyl explant on a first media, comprising thidiazuron at a concentration of between about 2.0 mg/L and 7.5 mg/L, and 2,4-D at a concentration of about 0.5 mg/L and 2.0 mg/L, to induce the production of a plurality of buds from at least one of said plurality of meristems;
   introducing exogenous DNA into at least one of the cells of said plurality of buds;
   removing said plurality of buds from said first media and transferring said plurality of buds to a second media suitable for induction of elongation of said buds into shoots;
   culturing said shoots to produce multiple transgenic wheat plants.

10. The method of claim 9, wherein said exogenous DNA is introduced via *Agrobacterium*-mediated transformation.

11. The method of claim 9, wherein said exogenous DNA is introduced via biolistic particle bombardment.

12. The method of claim 9, further comprising a step of selecting for plants containing the exogenous DNA.

* * * * *